United States Patent [19]

Stokes

[11] 4,269,198
[45] May 26, 1981

[54] BODY IMPLANTABLE LEAD

[75] Inventor: Kenneth B. Stokes, Minneapolis, Minn.

[73] Assignee: Medtronic, Inc., Minneapolis, Minn.

[21] Appl. No.: 106,854

[22] Filed: Dec. 26, 1979

[51] Int. Cl.$^3$ .............................................. A61N 1/04
[52] U.S. Cl. ................................................... 128/785
[58] Field of Search .................... 128/419 P, 784–786

[56] References Cited

U.S. PATENT DOCUMENTS

| | | | |
|---|---|---|---|
| 3,754,555 | 8/1973 | Schmitt ................................ | 128/785 |
| 3,814,104 | 6/1974 | Irnich et al. .......................... | 128/785 |
| 3,902,501 | 9/1975 | Citron et al. ......................... | 128/785 |
| 3,939,843 | 2/1976 | Smyth ................................... | 128/786 |
| 3,976,082 | 8/1976 | Schmitt ................................ | 128/785 |
| 4,033,357 | 7/1977 | Helland et al. ...................... | 128/785 |

*Primary Examiner*—William E. Kamm
*Attorney, Agent, or Firm*—Schroeder, Siegfried, Ryan, Vidas, Steffey & Arrett

[57] ABSTRACT

A body implantable lead of the type having a lead body, at least one electrode carried by the lead body and tissue engaging tines extending at an acute angle from the lead body at a location adjacent the electrode. The present invention correlates the tensile stiffness of the lead body with the stiffness of the tines to optimize the tine holding force. The tines provide an adequate holding force to minimize unintentional lead dislodgements without requiring in an excessive force for intentional dislodgement of the lead for repositioning. Tine length and the angle at which they extend from the lead body are also discussed as affecting the probability of tine engagement with cardiac structure as well as having an effect on the holding force. In a preferred embodiment, the lead body has a spring constant (as defined herein) of 2.0 lb-in./10 in. or less and a tine stiffness (also defined herein) of less than $5 \times 10^{-3}$ lb-in.$^2$. The tines are from two to six millimeters long and extend from the lead body at an angle from 30° to 80°. More preferably, the tine stiffness is $3 \times 10^{-3}$ lb-in.$^2$ or less with the tines being from four to six millimeters long and forming an angle with the lead body from 45° to 60°. In the preferred embodiments, the exposed surface of the lead body and the tines are formed of a body compatible urethane. In the most preferred embodiment, the tine stiffness is approximately $2.5 \times 10^{-3}$ lb-in.$^2$.

10 Claims, 1 Drawing Figure

BODY IMPLANTABLE LEAD

BACKGROUND OF PRIOR ART

Body implantable electrical leads for the delivery of stimulation energy to a desired body site are known to the prior art. Recent years have seen increased usage of transvenous leads which can deliver the stimulation energy to the desired body site while significantly lowering patient risk and morbidity. For example, the use of a transvenous/endocardial lead eliminates the necessity of a thoracotomy while delivering stimulation energy to the heart to provide a pacemaking function. Such endocardial leads may be used for sensing as well as pacing.

In many stimulation and sensing contexts, maintenance of a reliable electrical contact at the desired electrode site has proven difficult. To overcome this in the endocardial pacemaking environment, for example, pliant tines have been positioned adjacent the lead electrode to interact with cardiac structure to maintain the electrode in electrical contact with the heart tissue while allowing a removal of the electrode should that prove necessary, for repositioning, for example. An example of such tines employed for this purpose is disclosed in U.S. Pat. No. 3,902,501 issued Sept. 2, 1975, to Paul Citron and Eugene A. Dickhudt for ENDOCARDIAL ELECTRODE, which patent is commonly owned with the present invention and which is hereby incorporated herein by reference. In the incorporated patent, a plurality of tines extend from the lead body adjacent the tip and form an acute angle with the electrode body to cooperate with heart structure, particularly the trabeculae found in the right ventricle and atrial appendage, to maintain the electrode in position. The tines are disclosed as being pliant and non-conductive and serve the stated purpose of maintaining an electrode tip in electrical contact with heart tissue while allowing a removal of the electrode should that prove necessary. The tines are stated as making any angle with the lead body with an angle of approximately 45° maintaining the necessary electrical contact in a very efficient manner. Polyurethane is disclosed as a pliant material from which the tines may be formed while the catheter/conductor combination (lead body) is stated as being desirably as flexible as possible. However, no relationship is specified between the flexibility/stiffness of the tines relative to the flexibility/stiffness of the lead body.

Further examples of tined leads are disclosed in U.S. Pat. Nos. 3,939,843 issued Feb. 24, 1976, to Nicholas P. D. Smyth for TRANSVENOUS ELECTRODE and U.S. Pat. No. 4,003,357 issued July 5, 1977, to John R. Helland and Kenneth B. Stokes for NON-FIBROSING CARDIAC ELECTRODE, both of which are commonly owned with the present invention and which are hereby incorporated herein by reference. The Smyth patent discloses the use of polyurethane for the lead body insulating member and tines while the Helland et al patent discusses the superior elastomeric properties of a particular urethane relative to silicone rubber, a commonly used prior art lead body insulating member. However, neither of the latter incorporated patents disclose a stiffness/flexibility relationship between the tines and lead body that would optimize the holding power of the tines to facilitate lead removal for repositioning.

BRIEF SUMMARY OF THE INVENTION

The present invention provides a body implantable lead employing tines for electrode position maintenance that optimizes the holding power of the tines. The tensile stiffness of the lead body is correlated with the stiffness of the tines such that the tines provide an adequate holding force to minimize unintentional lead dislodgements without requiring an excessive force for intentional dislodgement of the lead for repositioning. As noted above, the use of tines, particularly in endocardial pacemaker leads, is known to the prior art for electrode position maintenance. However, the design of such prior art leads has focused on the interaction of the tines and the cardiac structure so as to minimize unintentional dislodgements. These efforts have been successful with the reoperation rate for a typical prior art lead being approximately five percent. In some instances, however, it is necessary to reposition a lead which requires an intentional dislodgement of the lead from the cardiac structure. For this purpose, the holding power of the prior art tined lead is often excessive and could result in damage to the cardiac structure.

The present invention recognizes that the forces imparted to a lead that have a tendency to dislodge the lead (forces from body movement, for example) are transmitted to the electrode site and that the stiffness of the lead body is a factor in that force transmission. Accordingly, the present invention provides a highly flexible lead body which itself can deform in response to extraneous forces to result in a lesser dislodgement force being imparted to the electrode. Accordingly, the holding power of the tines can be reduced to still provide an adequate holding power against unintentional dislodgements while requiring a lesser force than prior art leads for intentional dislodgement to facilitate repositioning. It has been found that for a lead body having a spring constant of less than 2.0 lb-in./10 in. (as defined below), a tine stiffness of less than $5 \times 10^{-3}$ lb-in.$^2$ (also defined below) optimizes the holding power of the tines relative to the lead body. In a preferred embodiment, the tines are from 2 mm to 6 mm long and extend from the lead body at an acute angle from 30° to 80°. More preferably, the tine stiffness is $3 \times 10^3$ lb-in.$^2$ or less, the tines being from 4 mm to 6 mm long and extending from the lead body at an acute angle from 45° to 60°. A body compatible urethane is the preferred material for the exposed surface of the lead body and the tines. The most preferred tine stiffness is approximately $2.5 \times 10^3$ lb-in.$^2$.

BRIEF DESCRIPTION OF THE DRAWING

The single FIGURE illustrates, in partial cutaway, a portion of a preferred embodiment of the present invention.

DETAILED DESCRIPTION OF THE DRAWING

Figure 1:
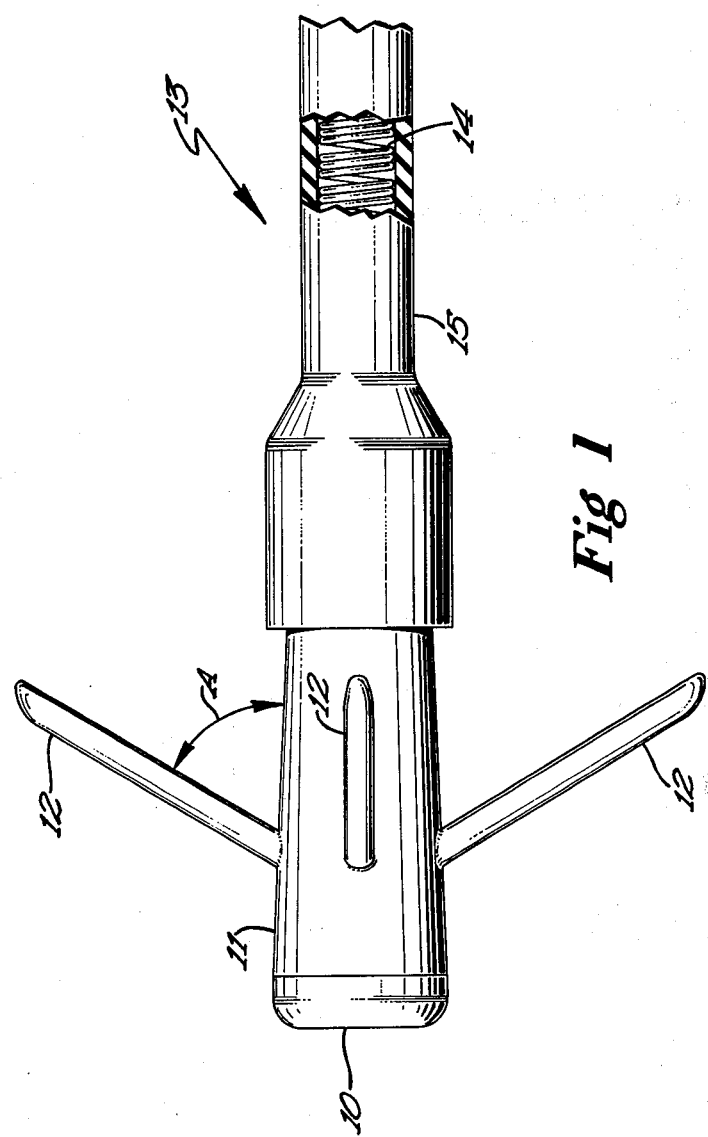

Referring now to the single FIGURE, there is illustrated a body implantable lead constructed in accordance with the present invention. A tip electrode 10 is provided in known manner at the distal end of the lead assembly and is formed of a conductive material to deliver stimulation energy to the desired body site. Adjacent the electrode 10 is a tine portion 11 which may be formed of a body compatible urethane and which may be generally tubular to overlie a conductor connected to the electrode 10. The tine portion 11 includes a plurality of tines 12 which extend from the tine portion 11 at an acute angle A. Preferably, angle A is from 30° to 80° and, most preferably, is from 45° to 60°. The tine portion 11 and integral tines 12 may be formed in any known manner, as by molding, for example.

The lead body is generally designated at 13 and is formed by a coiled conductor 14 and an overlying sheath 15. The coiled conductor 14 may be of any known design and preferably has a central aperture which will accept a stylet to provide stiffness during lead placement, in known manner. The lead body may also be non-linear such that stylet insertion will straighten the lead body to facilitate insertion, also in known manner. To facilitate the flexibility requirements of the present invention as well as for reliability considerations, the flexible conductor 14 may be a multifilar member, three filars being illustrated in the drawing. The conductor 14 is in electrical communication with the electrode 10 and a source of stimulation energy (not shown) for the delivery of stimulation energy to the desired body site. The sheath 15 may be a preformed tubular member, preferably of a body compatible urethane, to overlie the conductor 14 and provide electrical insulation therefor, in known manner.

In the prior art, many body stimulation leads are formed of a molded silicone. A preferable material for the sheath 15 and tine portion 11 and integral tines 12 is a body compatible urethane. This is the result of the flexibility requirements of the present invention as well as the fact that the urethanes are typically less thrombogenic than silicone and more resistant to tearing and cutting. In general, the physical characteristics of urethane are more suited to the present invention than is silicone, although silicone or any other body compatible material may be employed in practicing the present invention.

As noted above, the present invention correlates tensile stiffness of the lead body with the stiffness of the tines to provide a lead whose tines provide adequate holding power to minimize the number of unintentional dislodgements while reducing the force necessary to intentionally dislodge the tines to facilitate repositioning of the lead. The parameters by which the lead body tensile stiffness and tine stiffness are expressed are lead body "spring constant" and "tine stiffness." For the purposes of this specification and the appended claims, the term "spring constant" means the amount of force required to stretch a 10-inch length of lead one inch. The term "tine stiffness" is a measure of tine holding force and is dependent on the stiffness of the material (Young's modulus, E) and the moment of inertia (I) at the given cross-section. "Tine stiffness" equals EI. It has been found that a lead body having a spring constant of 2.0 lb-in./10 in. or less requires no more tine holding force than is provided by tines having a stiffness of less than $5 \times 10^{-3}$ lb-in.$^2$ with tines from 2 mm to 6 mm long which extend from the lead body at an acute angle from 30° to 80°. More preferably, the tine stiffness is $3 \times 10^{-3}$ lb-in.$^2$ or less with the tines being from 4 mm to 6 mm long and forming an angle with the lead body from 45° to 60°. In the most preferred embodiment, the tine stiffness is approximately $2.5 \times 10^{-3}$ lb-in.$^2$. The tine length and the angle between the tines and the lead body primarily affect the probability of the tines properly meshing with the cardiac structure. However, those parameters also appear to have some effect on the tine holding force and, for that reason, they are specified herein.

Obviously, many modifications and variations of the present invention are possible in light of the above teachings. For example, any body compatible material may be employed to form the exposed surface of the lead body and the tines, within the specified parameters. Further, any conductor configuration may be employed consistent with the flexibility requirements of the present invention. The number of tines may be varied according to preference and positioned around the periphery of a lead in accordance with known design considerations. In the illustrated embodiment, it is contemplated that four tines will be employed equidistantly positioned around the periphery of the lead. It is therefore to be understood that, within the scope of the appended claims, the invention may be practiced otherwise than as specifically described.

I claim:

1. In a body implantable lead of the type having a lead body, at least one electrode carried by said lead body and tine means extending at an acute angle from said lead body adjacent said electrode, the improvement wherein said lead body has a spring constant of less than 2.0 lb-in./10 in. and said tine means have a stiffness less than $5 \times 10^{-3}$ lb-in.$^2$, said tines being 2 mm to 6 mm long.

2. The body implantable lead of claim 1 wherein said tine means stiffness is $3 \times 10^{-3}$ lb-in.$^2$ or less.

3. The body implantable lead of claim 2 wherein said tine means are 4 mm to 6 mm long.

4. The body implantable lead of claim 3 wherein said acute angle is from 30° to 80°.

5. The body implantable lead of claim 4 wherein said acute angle is from 45° to 60°.

6. The body implantable lead of claim 5 wherein the exposed surface of said lead body comprises a body compatible urethane.

7. The body implantable lead of claim 6 wherein said tine means are formed of a body compatible urethane.

8. The body implantable lead of claim 7 wherein said tine means stiffness is approximately $2.5 \times 10^{-3}$ lb-in.$^2$.

9. The body implantable lead of claim 2 wherein said tine means stiffness is approximately $2.5 \times 10^{-3}$ lb-in.$^2$.

10. The body implantable lead of claim 9 wherein said tine means are 4 mm to 6 mm long.

* * * * *

UNITED STATES PATENT AND TRADEMARK OFFICE
CERTIFICATE OF CORRECTION

PATENT NO. : 4,269,198
DATED : May 26, 1981
INVENTOR(S) : Kenneth B. Stokes

It is certified that error appears in the above-identified patent and that said Letters Patent are hereby corrected as shown below:

Column 2, line 44, "$3 \times 10^3$ lb-in.$^2$" should be
--$3 \times 10^{-3}$ lb-in.$^2$--

Column 2, line 49, "$2.5 \times 10^3$ lb-in.$^2$" should be
--$2.5 \times 10^{-3}$ lb-in.$^2$--

Signed and Sealed this

Fifteenth Day of September 1981

[SEAL]

Attest:

GERALD J. MOSSINGHOFF

Attesting Officer      Commissioner of Patents and Trademarks